United States Patent
Barbie et al.

(10) Patent No.: US 10,472,599 B2
(45) Date of Patent: Nov. 12, 2019

(54) MICROFLUIDIC CELL CULTURE OF PATIENT-DERIVED TUMOR CELL SPHEROIDS

(71) Applicant: Dana-Farber Cancer Institute, Inc., Boston, MA (US)

(72) Inventors: David Barbie, Andover, MA (US); Amir Aref, Malden, MA (US); Thanh Barbie, Andover, MA (US); Russell W. Jenkins, Boston, MA (US); Kwok-kin Wong, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 182 days.

(21) Appl. No.: 15/540,346

(22) PCT Filed: Jan. 7, 2016

(86) PCT No.: PCT/US2016/012450
§ 371 (c)(1),
(2) Date: Jun. 28, 2017

(87) PCT Pub. No.: WO2016/112172
PCT Pub. Date: Jul. 14, 2016

(65) Prior Publication Data
US 2017/0369829 A1     Dec. 28, 2017

Related U.S. Application Data

(60) Provisional application No. 62/259,928, filed on Nov. 25, 2015, provisional application No. 62/100,607, filed on Jan. 7, 2015.

(51) Int. Cl.
| | |
|---|---|
| *G01N 31/00* | (2006.01) |
| *G01N 33/53* | (2006.01) |
| *C12M 3/06* | (2006.01) |
| *C12N 5/09* | (2010.01) |
| *G01N 33/50* | (2006.01) |

(52) U.S. Cl.
CPC ........... *C12M 23/16* (2013.01); *C12N 5/0693* (2013.01); *G01N 33/5082* (2013.01); *C12N 2503/02* (2013.01); *C12N 2513/00* (2013.01)

(58) Field of Classification Search
USPC ....................................................... 422/430
See application file for complete search history.

(56) References Cited

U.S. PATENT DOCUMENTS

| | | |
|---|---|---|
| 8,748,180 B2 | 6/2014 | Shuler et al. |
| 2009/0081639 A1 | 3/2009 | Hill et al. |
| 2010/0111768 A1 | 5/2010 | Banerjee et al. |
| 2010/0291584 A1 | 11/2010 | Tseng et al. |
| 2011/0159522 A1 | 6/2011 | Kamm et al. |
| 2012/0135452 A1 | 5/2012 | Shuler et al. |
| 2013/0143230 A1 | 6/2013 | Tolias et al. |
| 2014/0057311 A1 | 2/2014 | Kamm et al. |
| 2014/0221225 A1* | 8/2014 | Danen ................ G01N 33/5005 506/9 |
| 2019/0112666 A1 | 4/2019 | Barbie et al. |

FOREIGN PATENT DOCUMENTS

| | | |
|---|---|---|
| EP | 2741083 A1 | 6/2014 |
| WO | WO 2014/164464 A1 | 10/2014 |
| WO | WO 2016/112172 A1 | 7/2016 |

OTHER PUBLICATIONS

Serial No. PCT/US2016/012450, dated Apr. 8, 2016, International Search Report and Written Opinion.
Serial No. PCT/US2016/012450, dated Jul. 20, 2016, International Preliminary Report on Patentability.
Extended European Search Report for EP 167354301.8 dated Dec. 19, 2018.
International Search Report and Written Opinion for Application No. PCT/US2018/025390, dated Jun. 25, 2018.
Hasan et al., A Low-Cost Digital Microscope with Real-Time Fluorescent Imaging Capability. PLoS One. Dec. 15, 2016;11(12):e0167863. doi: 10.1371/journal.pone.0167863. eCollection 2016.
Perfetto et al., Amine reactive dyes: an effective tool to discriminate live and dead cells in polychromatic flow cytometry. J Immunol Methods. Jun. 30, 2016;313(1-2):199-208. Epub May 19, 2006.
Sabhachandani et al., Generation and functional assessment of 3D multicellular spheroids in droplet based microfluidics platform. Lab Chip. Feb. 7, 2016;16(3):497-505. doi: 10.1039/c51c01139f.
International Search Report and Written Opinion for PCT/US2016/012450 dated Apr. 8, 2016.
International Preliminary Report on Patentability for PCT/US2016/012450 dated Jul. 20, 2017.
Adams et al., Molecular regulation of angiogenesis and lymphangiogenesis. Nat Rev Mol Cell Biol. Jun. 2007;8(6):464-78.
Amman et al., Development of an innovative 3D cell culture system to study tumour-stroma interactions in non-small cell lung cancer cells. PLoS One. Mar. 24, 2014;9(3):e92511. doi: 10.1371/journal.pone.0092511. eCollection 2014.

(Continued)

*Primary Examiner* — Lisa V Cook
(74) *Attorney, Agent, or Firm* — Wolf, Greenfield & Sacks, P.C.

(57) ABSTRACT

Provided herein are methods for culturing patient-derived tumor cell spheroids in a three-dimensional microfluidic device. The method comprises mincing primary tumor sample in a medium supplemented with serum; treating the minced primary tumor sample with a composition comprising an enzyme; collecting tumor spheroids having a diameter of 10 μm to 500 μm from the enzyme treated sample; suspending the tumor spheroids in biocompatible gel; and culturing the tumor spheroids in a three dimensional microfluidic device. Methods for identifying an agent for treating cancer and microfluidic devices that allow for the simultaneous exposure of the cultured patient-derived primary tumor cell spheroids to a treatment of choice and to control treatment are also provided.

16 Claims, 6 Drawing Sheets

(56) References Cited

OTHER PUBLICATIONS

Aref et al., Screening therapeutic EMT blocking agents in a three-dimensional microenvironment. Integr Biol (Camb). Feb. 2013;5(2):381-9. doi: 10.1039/c2ib20209c.

Carbognin et al., Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. Jun. 18, 2015;10(6):e0130142. doi: 10.1371/journal.pone.0130142. eCollection 2015.

Crystal et al., Patient-derived models of acquired resistance can identify effective drug combinations for cancer. Science. Dec. 19, 2014;346(6216):1480-6. doi: 10.1126/science.1254721. Epub Nov. 13, 2014.

Gao et al., Organoid cultures derived from patients with advanced prostate cancer. Cell. Sep. 25, 2014;159(1):176-87. doi: 10.1016/j.cell.2014.08.016. Epub Sep. 4, 2014.

Gerdes et al., Highly multiplexed single-cell analysis of formalin-fixed, paraffin-embedded cancer tissue. Proc Natl Acad Sci U S A. Jul. 16, 2013;110(29):11982-7. doi: 10.1073/pnas.1300136110. Epub Jul. 1, 2013.

Lash et al., Comparison of three multiplex cytokine analysis systems: Luminex, SearchLight and Fast Quant. J Immunol Methods. Feb. 20, 2006;309(1-2):205-8. Epub Jan. 18, 2006.

Lo et al., The melanoma revolution: from UV carcinogenesis to a new era in therapeutics. Science. Nov. 21, 2014;346(6212):945-9. doi: 10.1126/science.1253735.

Morton et al., Establishment of human tumor xenografts in immunodeficient mice. Nat Protoc. 2007;2(2):247-50.

Seguin et al., An integrin $\beta_3$-KRAS-RalB complex drives tumour stemness and resistance to EGFR inhibition. Nat Cell Biol. May 2014;16(5):457-68. doi: 10.1038/ncb2953. Epub Apr. 20, 2014.

Siolas et al., Patient-derived tumor xenografts: transforming clinical samples into mouse models. Cancer Res. Sep. 1, 2013;73(17):5315-9. doi: 10.1158/0008-5472.CAN-13/1069. Epub Jun. 3, 2013.

Stanton et al., Current methods for assaying angiogenesis in vitro and in vivo. Int J Exp Pathol. Oct. 2004;85(5):233-48.

Taube et al., Differential Expression of Immune-Regulatory Genes Associated with PD-L1 Display in Melanoma: Implications for PD-1 Pathway Blockade. Clin Cancer Res. Sep. 1, 2015;21(17):3969-76. doi: 10.1158/1078-0432.CCR-15/0244. Epub May 5, 2015.

Tentler et al., Patient-derived tumour xenografts as models for oncology drug development. Nat Rev Clin Oncol. Apr. 17, 2012;9(6):338-50. doi: 10.1038/nrclinonc.2012.61.

Thiery., Epithelial-mesenchymal transitions in tumour progression. Nat Rev Cancer. Jun. 2002;2(6):442-54.

Yao et al., TGF-beta IL-6 axis mediates selective and adaptive mechanisms of resistance to molecular targeted therapy in lung cancer. Proc Natl Acad Sci U S A. Aug. 31, 2010;107(35):15535-40. doi: 10.1073/pnas.1009472107. Epub Aug. 16, 2010.

Yu et al., Cancer therapy. Ex vivo culture of circulating breast tumor cells for individualized testing of drug susceptibility. Science. Jul. 11, 2014;345(6193):216-20. doi: 10.1126/science.1253533.

Zhu et al., Inhibition of KRAS-driven tumorigenicity by interruption of an autocrine cytokine circuit. Cancer Discov. Apr. 2014;4(4):452-65. doi: 10.1158/2159-8290.CD-13-0646. Epub Jan. 20, 2014.

* cited by examiner

US 10,472,599 B2

MICROFLUIDIC CELL CULTURE OF PATIENT-DERIVED TUMOR CELL SPHEROIDS

RELATED APPLICATIONS

This application is a national stage filing under 35 U.S.C. § 371 of International Application PCT/US2016/012450, filed Jan. 7, 2016, and entitled "MICROFLUIDIC CELL CULTURE OF PATIENT-DERIVED TUMOR CELL SPHEROIDS" which claims priority under 35 U.S.C. § 119(e) to U.S. provisional application number 62/100,607, filed Jan. 7, 2015 and U.S. provisional application number 62/259,928, filed Nov. 25, 2015, the contents of each of which are incorporated herein by reference in their entirety.

GOVERNMENT SUPPORT

This invention was made with government support under K08 CA138918-01A1 and R01 CA190394-01 awarded by the National Institutes of Health. The government has certain rights in the invention.

BACKGROUND OF THE INVENTION

Cancer is the second leading cause of death in the United States. The complexity of most solid tumors limits the understanding of tumor biology and the development of new and improved treatments. The lack of robust in vitro and in vivo models that enable culture of primary human cancers and the reconstruction of the tumor microenvironment has hampered progress in understanding response to targeted therapeutics in real time. Most current studies rely on cancer cell line culture on plastic in 2-dimensions, or the cost and labor intensive generation of patient-derived xenograft (PDX) models in immunocompromised mice. Tumor models that more closely reflect the conditions in patients are required.

SUMMARY OF THE INVENTION

In some aspects, the present disclosure provides a method for culturing patient-derived tumor cell spheroids in a three-dimensional microfluidic device. The method comprises mincing a primary tumor sample in a medium supplemented with serum; treating the minced primary tumor sample with a composition comprising an enzyme; collecting tumor spheroids having a diameter of 10 μm to 500 μm from the enzyme treated sample; suspending the tumor spheroids in biocompatible gel; and culturing the tumor spheroids in a three dimensional microfluidic device.

In some embodiments, the primary tumor sample is frozen in a medium supplemented with serum and thawed prior to the mincing.

In some embodiments, the collected tumor spheroids are frozen in a freezing medium and then thawed before suspending in the biocompatible gel. In some embodiments, the minced primary tumor sample comprises tumor pieces in the size of about 1 mm.

In some embodiments, the tumor spheroids having a diameter of 10 μm to 500 μm are collected from the enzyme mix treated sample with the use of a sieve. In some embodiments, the tumor spheroids having a diameter of 40 μm to 100 μm are collected from the enzyme mix treated sample with the use of a sieve. In some embodiments, the tumor spheroids having a diameter of 10 μm to 500 μm are collected by sieving the enzyme mix treated sample via 500 μm and 10 μm cell strainers to yield tumor spheroids having a diameter of 10 μm to 500 μm.

In some embodiments, the enzyme is collagenase. In some embodiments, the composition comprising the enzyme mix comprises a serum-supplemented culture medium, insulin, a corticosteroid, an antibiotic, collagenase and optionally a growth factor. In some embodiments, the corticosteroid is hydrocortisone.

In some embodiments, the minced primary tumor sample is treated with the composition comprising the enzyme in an amount or for a time sufficient yield a partial digestion of the minced primary tumor sample.

In some embodiments, the minced primary tumor sample is treated with the enzyme mix for 30 minutes to 15 hours at a temperature of 25° C. to 39° C. In some embodiments, the minced primary tumor sample is treated with the composition comprising the enzyme for 30 minutes to 60 minutes at a temperature of 37° C.

In some embodiments, the biocompatible gel is collagen or BD Matrigel™ Matrix Basement Membrane. In some embodiments, the biocompatible gel is a fibrin hydrogel. In some embodiments, the fibrin hydrogel is generated from thrombin treatment of fibrinogen.

In some embodiments, the primary tumor sample is obtained from a subject. In some embodiments, the primary tumor sample is a patient derived xenograft (PDX).

In some embodiments, the three dimensional microfluidic device comprises one or more fluid channels flanked by one or more gel cage regions, wherein the one or more gel cage regions comprises the biocompatible gel in which the tumor spheroids are embedded, and wherein the device recapitulates in vivo tumor microenvironment.

In some embodiments, the three dimensional microfluidic device comprises a substrate comprised of an optically transparent material and further comprising i) one or more fluid channels; ii) one or more fluid channel inlets; iii) one or more fluid channel outlets; iv) one or more gel cage regions; and v) a plurality of posts; wherein all or a portion of each gel cage region is flanked by all or a portion of one or more fluid channels, thereby creating one or more gel cage region-fluid channel interface regions; each gel cage region comprises at least one row of posts which forms the gel cage region; and the one or more gel cage region has a height of at least 500 μm. In some embodiments, the one or more gel cage region has a height of 600 μm, 700 μm, 800 μm, 900 μm, or 1000 μm. In some embodiments, the one or more gel cage region has a height sufficient for at least 200-1000 μm above the tumor cell spheroids.

In some embodiments, the gel cage region has a cuboidal shape. In some embodiments, the device comprises 2 gel cage regions. In some embodiments, a portion of a first gel cage region is flanked by a portion of a second gel cage region, thereby creating a gel cage region-gel cage region interface region. In some embodiments, the first and second gel cage regions are separated by a barrier which does not allow intermixing between components present in the two gel cage regions.

In some aspects, the present disclosure provides a method for identifying an agent for treating cancer. The method comprises culturing patient-derived tumor cell spheroids in a three-dimensional microfluidic device as described herein in the presence and absence of a first test agent and detecting a change in the tumor cell spheroid culture indicative of a response likely to result in reduction in proliferation and/or dispersion of the tumor cell spheroids in the presence of the first test agent as compared to the absence of the first test agent; wherein if the change in the tumor cell spheroid culture is indicative of a response likely to result in a reduction in the proliferation and/or dispersion of the tumor cell spheroids in the presence of the first test agent as compared to the absence of the first test agent, then the first test agent can be used to treat cancer.

In some embodiments the method comprises, culturing patient-derived tumor cell spheroids in the presence of the test agent comprises introducing the test agent into the one or more fluid channels of a device described herein, wherein the one or more gel cage regions of the device comprises a gel in which the tumor spheroids are embedded; and culturing the tumor spheroids under suitable culture conditions.

In some embodiments, the change in the tumor cell spheroid culture is detected chemically, physically, or a combination thereof. In some embodiments, the change in the tumor cell spheroid culture is detected visually. In some embodiments, the proliferation and/or dispersion of the tumor cell spheroids is determined using by confocal imaging.

In some embodiments, the change in the tumor cell spheroid culture is a decrease in size and/or number of cells of one or more tumor cell spheroids in the culture.

In some embodiments, the change in the tumor cell culture is detected chemically. In some embodiments, the change in the tumor cell spheroid culture is determined by detection of the presence of a biological molecule secreted into the culture supernatant. In some embodiments, the biological molecule is a protein, carbohydrate, lipid, nucleic acid, metabolite, or a combination thereof. In some embodiments, the biological molecule is a cytokine or a chemokine.

In some embodiments, the method includes obtaining a sample of tumor cell spheroid culture supernatant.

In some embodiments, the method includes detecting a cytokine profile or chemokine profile in the tumor cell spheroid culture supernatant.

In some embodiments, the test agent inhibits epithelial-mesenchymal transition (EMT).

In some embodiments, the first test agent is a small molecule, a nucleic acid molecule, an RNAi agent, an aptamer, a protein or a peptide, an antibody or antigen-binding antibody fragment, a ligand or receptor-binding protein, a gene therapy vector, or a combination thereof.

In some embodiments, the first test agent is a chemotherapeutic agent, an immunomodulatory agent, or radiation. In some embodiments, the first test agent is a chemotherapeutic agent selected from the group consisting of an alkylating agent, an antimetabolite, an anthracycline, a proteasome inhibitor, and an mTOR inhibitor.

In some embodiments, the first test agent is an immune modulator. In some embodiments, the first test agent is an immune checkpoint inhibitor.

In some embodiments, the patient-derived tumor cell spheroids are cultured in the presence of a second test agent. In some embodiments, the second test agent is an anti-cancer agent.

In some embodiments, the anti-cancer agent is a chemotherapeutic agent, an immunomodulatory agent, or radiation. In some embodiments, the second test agent is an immune modulator. In some embodiments, the second test agent is an immune checkpoint inhibitor.

In embodiments, any one of the first test agents may be combined with any one of the second test agents.

In some aspects, the present disclosure provides a microfluidic device. The device comprises a substrate comprised of an optically transparent material and further comprising i) a first gel cage region and a second gel cage region; ii) a first fluid channel and a second fluid channel; iii) one or more fluid channel inlets; iv) one or more fluid channel outlets; and v) a plurality of posts; wherein a portion of the first gel cage region is flanked by a portion of the second gel cage region, thereby creating a gel cage region-gel cage region interface region; wherein the first and second gel cage regions are separated by a barrier which does not allow intermixing between components present in the two gel cage regions; wherein a portion of the first gel cage region is flanked by all or a portion of the first fluid channel, thereby creating a first gel cage region-fluid channel interface region; wherein a portion of the second gel cage region is flanked by all or a portion of the second fluid channel, thereby creating a second gel cage region-fluid channel interface region; and, wherein each gel cage region comprises one row of posts along the length of the gel cage region at the first and second gel cage region-fluid channel interfaces.

In some embodiments, each gel cage region has a height of at least 500 μm. In some embodiments, each gel cage region has a height of 600 μm, 700 μm, 800 μm, 900 μm, or 1000 μm. In some embodiments, each gel cage region has a cuboidal shape.

In some aspects, the present disclosure provides a method for identifying an agent for treating cancer, the method comprising: a) introducing a test agent into the first fluid channel of a device as described herein, wherein each gel cage region of the device comprises a gel in which the tumor spheroids are embedded; and b) detecting a signal in the first cage region indicative of a response likely to result in a reduction in proliferation and/or dispersion of the tumor cell spheroids in the first gel cage region as compared that in the second gel cage region; wherein if the signal in the first cage region is indicative of a response likely to result in a reduction in the proliferation and/or dispersion of the tumor cell spheroids in the first gel cage region as compared that in the second gel cage region, then the agent can be used to treat cancer.

In some aspects, the present disclosure provides a method for treating cancer in a subject, the method comprising: a) obtaining a tumor sample from the subject; b) identifying an agent that can be used to treat cancer in the subject according to a method described herein; and c) administering the agent to the subject.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE INVENTION

Figure 1:
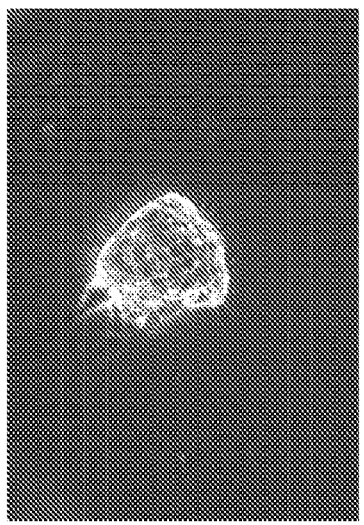
FIG. 1 shows mesothelioma cells are induced to disperse by co-culture with human umbilical vein endothelial cells (HUVECs).
Figure 1:
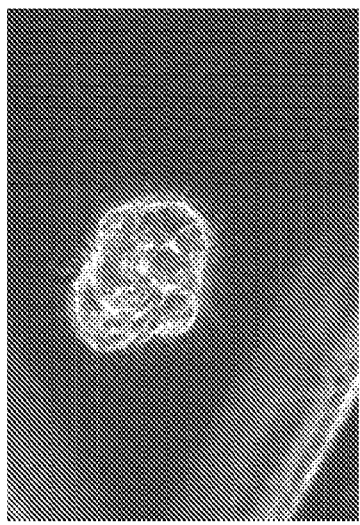
Figure 1:
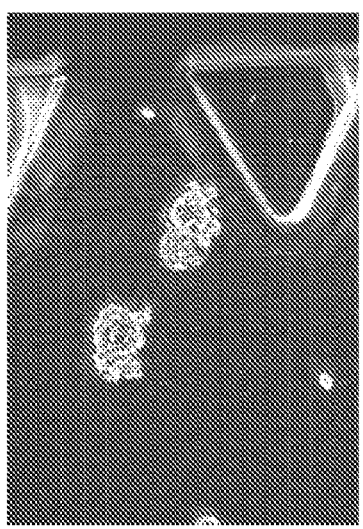
Figure 1:
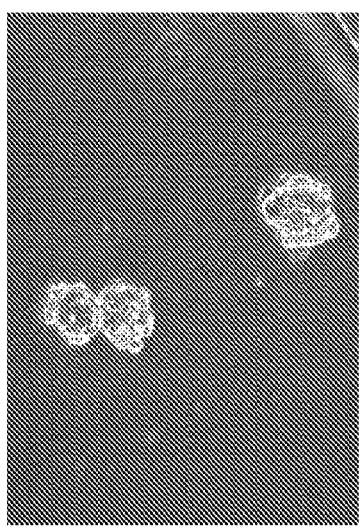

One major factor in the lack of success in improving patient prognosis and survival after cancer diagnosis is the limitation of current in vitro and in vivo cancer models. The data obtained from studies using the current models translates poorly into human clinical practice because of their lack of concordance with the situation present in the human body (Staton C A, Stribbling S M, Tazzyman S, Hughes R, Brown N J, Lewis C E. Current methods for assaying angiogenesis in vitro and in vivo. Int J Exp Pathol 2004; 85:233-48). For example, a Boyden chamber test, commonly used to study the invasive properties of a neoplastic cell population of interest, measures the ability of cells to migrate across an artificial barrier. However, a neoplastic cell will never encounter such an artificial barrier in a native environment. Human tumor cells in vivo typically form three-dimensional structures, with drug, metabolite, and cell-cell interaction kinetics much different from those in two-dimensional culture.

While patient-derived xenografts (PDX) represent a significant advance over traditional cancer cell line-based studies, this model system too has a number of important limitations. These include the need for expensive cohorts of immunocompromised mice, a long period time required to establish sufficient numbers of tumors, and, because of this problem of scale, a limited ability to test multiple drug concentrations and/or combinations. These challenges pose a major hurdle for using this system to match appropriate therapies to individual patients, the overall goal of personalized cancer medicine.

Some aspects of this disclosure address and overcome at least some of the shortcomings of the current in vitro and in vivo models of cancer described above. Some aspects of the present disclosure are based on the surprising discovery that primary tumor specimens can be isolated and grown in a three-dimensional (3D) microfluidic culture device. This technology enables the culture of individual patient tumors and real time evaluation of novel therapeutics in an unprecedented fashion. Prior to the instant disclosure, it was not known whether tumor spheroids obtained from primary tumor would grow in vitro in a 3D microfluidic device. In fact, previous attempts to grow micro-dissected tumor samples in a 3D microfluidic device were unsuccessful. The present disclosure provides, in some aspects, methods to isolate and culture tumor spheroids from primary human tumors. In some aspects, the technology recapitulates the tumor microenvironment, enabling cell-cell interactions that reflect the endothelial-cancer cell interface, and allowing controlled analysis of growth factor and cytokine mediated effects.

In some aspects, the methods described herein enable the analysis of conditioned media during co-culture of tumor spheroids with endothelial cells, providing a unique opportunity to measure primary tumor cytokine production. For example, media exchange every 2 days during spheroid culture provides the opportunity to store conditioned media for analysis of individual cytokines, such as IL-6 by enzyme-linked immunosorbent assay (Zhu et al., Cancer Discov 2014 Apr.; 4 (4):452-65; incorporated herein by reference in its entirety) or broad cytokine profiling using luminex multiplex technology, for example (Lash et al., J Immunol Methods 2006 Feb. 20;309(1-2):205-8; incorporated herein by reference in its entirety). Accordingly, aspects of the present disclosure relate to methods for culturing patient-derived tumor cell spheroids in a three-dimensional microfluidic device. The method comprises mincing a primary tumor sample in a medium supplemented with serum; treating the minced primary tumor sample with a composition comprising an enzyme; collecting tumor spheroids having a diameter of 10 μm to 500 μm from the enzyme treated sample; suspending the tumor spheroids in biocompatible gel; and culturing the tumor spheroids in a three dimensional microfluidic device.

As used herein, the term "tumor" refers to a neoplasm, i.e., an abnormal growth of cells or tissue and is understood to include benign, i.e., non-cancerous growths, and malignant; i.e., cancerous growths including primary or metastatic cancerous growths.

Examples of neoplasms include, but are not limited to, mesothelioma, lung cancer (e.g., small-cell lung cancer, non-small cell lung cancer), skin cancer (e.g., melanoma), stomach cancer, liver cancer, colorectal cancer, breast cancer, pancreatic cancer, prostate cancer, blood cancer, bone cancer, bone marrow cancer, and other cancers.

The term "tumor spheroid," or "tumor cell spheroid" as used herein, refers to an aggregation of tumor cells constituting a small mass, or lump of tumor cells. In some embodiments, tumor spheroids are less than about 3 cm, less than about 2 cm, less than about 1 cm, less than about 5 mm, less than about 2.5 mm, less than about 1 mm, less than about 100 μm, less than about 50 μm, less than about 25 μm, less than about 10 μm, or less than about 5 μm in diameter. In some embodiments, the tumor spheroids have a diameter of 10 μm to 500 μm. In some embodiments, the tumor spheroids have a diameter of 40 μm to 100 μm. In some embodiments, the tumor spheroids have a diameter of 40 μm to 70 μm.

The term "primary tumor sample" as used herein refers to a sample comprising tumor material obtained from a subject having cancer. The term encompasses tumor tissue samples, for example, tissue obtained by surgical resection and tissue obtained by biopsy, such as for example, a core biopsy or a fine needle biopsy. The term also encompasses patient derived xenograft (PDX). Patient derived xenografts are created when cancerous tissue from a patient's primary tumor is implanted directly into an immunodeficient mouse (see, for example, Morton C L, Houghton P J (2007). "Establishment of human tumor xenografts in immunodeficient mice". Nature Protocols 2 (2): 247-50; Siolas D, Hannon G J (September 2013). "Patient-derived tumor xenografts: transforming clinical samples into mouse models". Cancer Research 73 (17): 5315-9). PDX mirrors patients' histopathological and genetic profiles. It has improved predictive power as preclinical cancer models, and enables the true individualized therapy and discovery of predictive biomarkers.

In some embodiments, the subject is a human. In some embodiments, the subject is a non-human mammal or a non-human vertebrate. In some embodiments, the subject is laboratory animal, a mouse, a rat, a rodent, a farm animal, a pig, a cattle, a horse, a goat, a sheep, a companion animal, a dog a cat, or a guinea pig.

In some embodiments, the primary tumor sample is collected in a serum-supplemented medium, for example but not limited to, RPMI medium supplemented with 10% fetal bovine serum. The sample is then minced, i.e, cut or chopped into tiny pieces. In some embodiments, the sample is minced on ice. In some embodiments, the minced primary tumor sample comprises tumor pieces in the size of about 3 mm, 2.5 mm, 2.0 mm, 1.5 mm, 1.0 mm, 0.5, or 0.25 mm.

In some embodiments, the primary tumor sample is not frozen and thawed.

In some embodiments, minced primary tumor sample is frozen in a medium supplemented with serum and thawed prior to treating with the composition comprising the enzyme. In some embodiments, the minced primary tumor sample is frozen for at least 6 hours 12 hours, 24 hours, 2 days, 1 week or one month. In some embodiments, the minced primary tumor sample is frozen at −80° C. In some embodiments, the minced primary tumor sample is frozen in liquid nitrogen. In some embodiments, the minced primary tumor sample is frozen in a medium supplemented with serum. In some embodiments, the minced primary tumor sample is frozen in a mixture containing serum and solvent such as Dimethyl sulfoxide (DMSO). In some embodiments, the minced primary tumor sample is frozen in a mixture containing fetal bovine serum and Dimethyl sulfoxide (DMSO).

In some embodiments, the frozen minced primary tumor sample is thawed, i.e., defrosted, before treating the sample with a composition comprising an enzyme. In some embodiments, the minced primary tumor sample is thawed in a water bath kept at about 37° C. (e.g., 35° C., 36° C., 37° C., 38° C., or 39° C.). In some embodiments, the minced primary tumor sample is thawed at room temperature.

The minced primary tumor sample is treated with an enzyme mix to digest the tumor samples. In some embodiments, the composition comprising an enzyme includes collagenase. In some embodiments, the composition comprising an enzyme includes a serum-supplemented culture medium, insulin, one or more corticosteroids, one or more antibiotics, collagenase and optionally one or more growth factors. Serum-supplemented culture media, corticosteroids, antibiotics, and growth factors are well-known in the art. In some embodiments, the composition comprising an enzyme comprises DMEM or RPMI, fetal bovine serum, insulin, epidermal growth factor, hydrocortisone, Penicillin and/or Streptomycin, and collagenase. In some embodiments, the composition comprising an enzyme comprises further comprises a buffering agent such as 4-(2-hydroxyethyl)-1-piperazineethanesulfonic acid (HEPES).

"Treating the minced primary tumor sample with a composition comprising an enzyme" comprises incubating the minced tumor samples with the enzyme composition for at least 1 hour. In some embodiments, the minced tumor samples are incubated with the enzyme mix for at least 2 hours, at least 4 hours, at least 6 hours, at least 8 hours, at least 10 hours, at least 12 hours, at least 15 hours or at least 24 hours. In some embodiments, the minced primary tumor sample is incubated with the enzyme mix at 25° C., 26° C., 27° C., 28° C., 29° C., 30° C., 31° C., 32° C., 33° C., 34° C., 35° C., 36° C., 37° C., 38° C., or 39° C. In some embodiments, the minced primary tumor sample is incubated with the enzyme mix at 37° C.

In some embodiments, the minced primary tumor sample is treated with the composition comprising the enzyme in an amount or for a time sufficient yield a partial digestion of the minced primary tumor sample. In some embodiments, the minced primary tumor sample is treated with the composition comprising the enzyme for 30 minutes to 15 hours at a temperature of 25° C. to 39° C.

Collecting tumor spheroids from the enzyme mix treated sample comprises centrifuging and washing the sample at least twice followed by isolating the digested tumor spheroids of the desired size. In some embodiments, the enzyme mix treated sample is centrifuged and washed using phosphate buffered saline (PBS) at least twice. Tumor spheroids of the desired size are collected using sieves. In some embodiments, the tumor spheroids having a diameter of 10 μm, 50 μm, 100 μm, 200 μm, 300 μm, 400 μm, 450 μm, and 500 μm are collected from the enzyme mix treated sample with the use of a sieve. In some embodiments, the tumor spheroids having a diameter of 40 μm to 100 μm are collected from the enzyme mix treated sample with the use of a sieve. In some embodiments, the tumor spheroids having a diameter of 40 μm, 50 μm, 60 μm and 70 μm are collected from the enzyme mix treated sample with the use of a sieve.

The tumor spheroids having a desired diameter are collected by sieving the enzyme mix treated sample through cell strainers. In some embodiments, the tumor spheroids having a diameter of 10 μm to 500 μm are collected by sieving the enzyme mix treated sample via 500 μm and 10 μm cell strainers to yield tumor spheroids having a diameter of 10 μm to 500 μm. In some embodiments, the tumor spheroids having a diameter of 40 μm to 100 μm are collected by sieving the enzyme mix treated sample via 100 μm and 40 μm cell strainers to yield tumor spheroids having a diameter of 10 μm to 500 μm. The tumor spheroids of the desired diameter are collected and suspended in a biocompatible gel. Examples of biocompatible gel include collagen, BD Matrigel™ Matrix Basement Membrane, or fibrin hydrogel (e.g., fibrin hydrogel generated from thrombin treatment of fibrinogen).

In some embodiments, the collected tumor spheroids are not frozen and then thawed before suspending in the biocompatible gel.

In some embodiments, the collected tumor spheroids are frozen in a freezing medium and then thawed before suspending in the biocompatible gel. In some embodiments, the collected tumor spheroids are frozen for at least 6 hours 12 hours, 24 hours, 2 days, 1 week or one month. In some embodiments, the collected tumor spheroids are frozen at −80° C. In some embodiments, the collected tumor spheroids are frozen in liquid nitrogen. In some embodiments, the collected tumor spheroids are frozen at −80° C. overnight, and then transferred to liquid nitrogen for storage. In some embodiments, the collected tumor spheroids are frozen in a medium supplemented with serum. In some embodiments, the collected tumor spheroids are frozen in a mixture containing culture medium such as DMEM or RPMI, fetal bovine serum and solvent such as Dimethyl sulfoxide (DMSO). The frozen spheroids are thawed, for example overnight at 4° C., and then suspended in the biocompatible gel.

The tumor spheroids are cultured, i.e., grown, in a three dimensional (3D) microfluidic device. In some embodiments, the tumor spheroids are cultured with endothelial cells, such as human umbilical vein endothelial cells (HU- VECs). In some embodiments, the tumor spheroids are cultured with or without endothelial cells for at least 1 day, at least 2 days, at least 4 days, at least 6 days, at least 1 week, or at least 2 weeks.

3D microfluidic devices are known in the art and include, for example, but not limited to, the devices described in US 2013/0143230, EP2741083, US 2014/0057311, and U.S. Pat. No. 8,748,180, the disclosures of which are incorporated by reference herein.

In some embodiments, a 3D microfluidic device refers to a device that comprises one or more fluid channels flanked by one or more gel cage regions, wherein the one or more gel cage regions comprises the biocompatible gel in which the tumor spheroids are embedded, and wherein the device recapitulates, i.e., mimics, the in vivo tumor microenvironment. In order to facilitate visualization, the microfluidic device is typically comprised of a substrate that is transparent to light, referred to herein as "an optically transparent material". As will be appreciated by those of skill in the art, suitable optically transparent materials include polymers, plastic, and glass. Examples of suitable polymers are polydimethylsiloxane (PDMS), poly(methyl methacrylate) (PMMA), polystyrene (PS), SU-8, and cyclic olefin copolymer (COC). In some embodiments, all or a portion of the device is made of a biocompatible material, e.g., the material is compatible with, or not toxic or injurious to, living material (e.g., cells, tissue).

The fluid channel can be used to contain a (one or more) fluid (e.g., cell culture media), cells such as endothelial cells, cellular material, tissue and/or compounds (e.g., drugs) to be assessed, while the gel cage regions may be used to contain a gel (e.g., biologically relevant gel, such as collagen, Matrigel™, or fibrin hydrogel (e.g., fibrin hydrogel generated from thrombin treatment of fibrinogen)). In some embodiments, the 3D microfluidic device comprises the device described in US 2014/0057311, the disclosure of which is incorporated by reference herein. In particular, paragraphs [0056] to [0107] which describe the regions, channels, chambers, posts, and arrangement of posts, and paragraphs [0127] to [0130] which describe the methods of making the device are incorporated by reference herein.

The original gel region described in US 2014/0057311, and incorporated by reference herein, was designed to study biology of individual cell lines, which requires a relatively small volume. This small volume is inadequate to capture whole tissue sections (even when micro-dissected). Accordingly, in some embodiments, the gel cage region has a height of 500 µm, 600 µm, 700 µm, 800 µm, 900 µm, or 1000 µm. This device can accommodate>10, >20, >30, >40 and>50 spheroids, which is necessary to capture the full heterogeneity of the primary tumor. The method of claim 18, wherein the one or more gel cage region has a height sufficient for at least 200-1000 µm above the tumor cell spheroids.

In some embodiments, the gel cage region has a cuboidal shape. The cuboidal shape is better suited to accommodate the shape of primary tissue sections, and concentrates spheroids, which facilitates extraction after endothelial co-culture, and implantation into immune-compromised mice for tumor tissue expansion.

Aspects of the disclosure also relate to a microfluidic device that allows for the simultaneous exposure of the cultured patient-derived primary tumor cell spheroids to a treatment of choice and to control treatment. Thus, the device provides a built-in internal control. The device comprises a substrate comprised of an optically transparent material and further comprising i) a first gel cage region and a second gel cage region
ii) a first fluid channel and a second fluid channel;
iii) one or more fluid channel inlets;
iv) one or more fluid channel outlets; and
v) a plurality of posts;
wherein
a portion of the first gel cage region is flanked by a portion of the second gel cage region, thereby creating a gel cage region-gel cage region interface region;
the first and second gel cage regions are separated by a barrier which does not allow intermixing between components present in the two gel cage regions;
a portion of the first gel cage region is flanked by all or a portion of the first fluid channel, thereby creating a first gel cage region-fluid channel interface region;
a portion of the second gel cage region is flanked by all or a portion of the second fluid channel, thereby creating a second gel cage region-fluid channel interface region; and
each gel cage region comprises one row of posts along the length of the gel cage region at the first and second gel cage region-fluid channel interfaces.

Because the first and second gel cage regions are separated by a barrier, no intermixing between components present in the two gel cage regions takes place, i.e., the barrier is impermeable to cells, cellular material, molecules secreted by the cells, tissue and/or compounds (e.g., drugs). In some embodiments, the barrier is made of suitable impermeable material, such as but not limited to, polydimethylsiloxane (PDMS), poly(methyl methacrylate) (PMMA), polystyrene (PS), SU-8, and cyclic olefin copolymer (COC). The gel-cage-fluid channel interfaces, on the other hand, are lined by a row of posts and when a gel is present in the gel cage regions, the gel can be contacted with any fluid present in the fluid channels.

In some embodiments, the gel cage regions of the device have a height of 500 µm, 600 µm, 700 µm, 800 µm, 900 µm, or 1000 µm. In some embodiments, the gel cage regions of the device have a cuboidal shape. In some embodiments, the device is used to culture tumor spheroids using the methods described herein.

It was not known whether tumor spheroids obtained from primary tumor would grow in vitro in a 3D microfluidic device in the presence of a test agent, e.g., enabling the identification of an agent as an anti-cancer agent. This was particularly the case in connection with successfully culturing tumor spheroids in the presence of immune check point inhibitors. Aspects of the disclosure also include methods for of identifying an agent for treating cancer. In some embodiments, the method for identifying an agent for treating cancer, comprises culturing patient-derived tumor cell spheroids in a three-dimensional microfluidic device as described herein in the presence and absence of a test agent, detecting a change in the tumor cell spheroid culture indicative of a result likely to yield a reduction in proliferation and/or dispersion of the tumor cell spheroids in the presence of the first test agent as compared to the absence of the first test agent; wherein if the change in the tumor cell spheroid culture is indicative of a result likely to yield reduction in the proliferation and/or dispersion of the tumor cell spheroids in the presence of the first test agent as compared to the absence of the first test agent, then the first test agent can be used to treat cancer.

In some embodiments, the method for identifying an agent for treating cancer, comprises a) introducing a test agent into the first fluid channel of the device described herein, wherein each gel cage region of the device comprises a gel in which the tumor spheroids are embedded; and b)

detecting a change in the tumor cell spheroid culture indicative of a reduction in proliferation and/or dispersion of the tumor cell spheroids in the first gel cage region as compared that in the second gel cage region; wherein if the change in the tumor cell spheroid culture is indicative of a reduction in the proliferation and/or dispersion of the tumor cell spheroids in the first gel cage region as compared that in the second gel cage region, then the agent can be used to treat cancer.

"Culturing patient-derived tumor cell spheroids in the presence of the test agent" comprises introducing the test agent into the one or more fluid channels of the device described herein, wherein the one or more gel cage regions of the device comprises a gel in which the tumor spheroids are embedded; and culturing the tumor spheroids under suitable culture conditions. Suitable conditions include growing the tumor cell spheroids under standard cell culture conditions (e.g. at 37° C. in a humidified atmosphere of >80% relative humidity air and 5 to 10% $CO_2$).

In some embodiments, the tumor spheroids are cultured in the presence of endothelial cells. In some embodiments, the tumor spheroids are cultured in the presence of endothelial cells for at least 1 day, at least 2 days, at least 4 days, at least 6 days, at least 1 week, or at least 2 weeks before the test agent is introduced into the one or more fluid channels of the device described herein. In some embodiments, the tumor spheroids are cultured in the presence of endothelial cells for at least 1 week before the test agent is introduced into the one or more fluid channels of the device described herein. This allows the tumor spheroids and the endothelial cells to form a tumor tissue network.

Changes in the tumor cell spheroid culture which predict or demonstrate a reduction in proliferation and/or dispersion of the tumor cell spheroids in the presence or absence of the test agent can be detected using known methods in the art, such as, chemical or physical methods, or a combination thereof. For example, a change in the tumor cell spheroid culture can be detected visually, e.g., using confocal microscopy imaging. The images obtained can be analyzed as described in Aref et al. Integr Biol (Camb). 2013 February; 5(2):381-9, the disclosure of which is incorporated by reference in its entirety. In particular, the paragraphs on pages 387-388 relating to image acquisition and analysis (normalized dispersion, $\Delta/\Delta_0$, and normalized cell number ($N/N_0$)) are incorporated by reference in their entirety. In some embodiments, viability of the tumor cells is determined using propidium iodide, annexin V, or cellular ATP content, as disclosed by Amman et al. PLoS One 2014 Mar. 24; 9(3):e92511 and Zhu et al., Cancer Discov 2014 Apr; 4(4):452-65 (each incorporated herein by reference in its entirety.

In some embodiments, the change in the tumor cell spheroid culture is a clustering of immune cells around one or more tumor cell spheroids in the culture. In some embodiments, the change in the tumor cell spheroid culture is a decrease in size and/or number of cells of one or more tumor cell spheroids in the culture.

In some embodiments, the change in the tumor cell culture is detected chemically. For example, in some embodiments, the change in the tumor cell spheroid culture is determined by detection of the presence of a biological molecule secreted into the culture supernatant. In some embodiments, the biological molecule is a protein, carbohydrate, lipid, nucleic acid, metabolite, or a combination thereof. In some embodiments, the biological molecule is a chemokine or a cytokine. In some embodiments, the biological molecule is known to be associated with activation of the immune system or otherwise an enhancement of the immune response.

In some embodiments, the detected biological molecule(s) involves single cell sequencing of T cell receptors on tumor spheroid associated CD4 and CD8 T cells that become activated in the device.

In some embodiments, a method of the invention comprises obtaining a sample of tumor cell spheroid culture supernatant. In some embodiments, a method of the invention comprises detecting a secreted biological molecule or a profile of secreted biological molecules, e.g., a cytokine profile or chemokine profile, in the tumor cell spheroid culture supernatant.

Methods for detecting secreted biological molecules are known in the art. In some embodiments, a multiplex profiling assay is used to determine a profile of secreted biological molecules. For example, a Bio-Plex® Multiplex Assay (BioRad) may be used. The Bio-Plex® Multiplex Assay is able to distinguish up to 100 different families of color-coded, monodisperse polystyrene beads, each bearing a different homogeneous capture assay (but all using the same signal molecule) in a single 50 µl sample. This high degree of multiplexing dramatically increases the amount of useful information from rare or volume-limited samples. The Bio-Plex® assays are built around the well-known Luminex xMAP technology using a bead-based flow cytometric platform dedicated to multiplex analysis Similar to ELISA, a majority of assays are designed according to a capture sandwich immunoassay format. Briefly, the capture antibody-coupled beads are first incubated with antigen standards or samples for a specific time. The plate is then washed to remove unbound materials, followed by incubation with biotinylated detection antibodies. After washing away the unbound biotinylated antibodies, the beads are incubated with a reporter streptavidin-phycoerythrin conjugate (SA-PE). Following removal of excess SA-PE, the beads are passed through the array reader, which measures the fluorescence of the bound SA-PE. The substrate for the antibody sandwich is the bead. xMAP assays may contain nonmagnetic or magnetic beads as substrates. Magnetic COOH beads are unique in that they exhibit both fluorescent and magnetic properties. The beads are stained with a fluorescent dye formulation proprietary to Luminex. The staining process involves swelling the bead particles in a dye containing solvent, which allows the dye molecules to infuse into the coating or the polymer layer. Removal of the solvent in a subsequent step shrinks the beads and traps the dye molecules within the bead particles. The magnetite layer of the bead is one important feature that allows many of the newer assays to be automated with robotic wash stations.

In some embodiments, the detected biological molecule(s) include one or more of the following: Hu 6Ckine/CCL21, Hu BCA-1/CXCL13, Hu CTACK/CCL27, Hu ENA-78/CXCLS, Hu Eotaxin/CCL11, Hu Eotaxin-2/CCL24, Hu Eotaxin-3/CCL26, Hu Fractalkine/CX3CL1, Hu GCP-2/CXCL6, Hu GM-CSF, Hu Gro-a/CXCL1, Hu Gro-b/CXCL2, Hu I-309/CCL1, Hu IFN-g, Hu IL-10, Hu IL-16, Hu IL-lb, Hu IL-2, Hu IL-4, Hu IL-6, Hu IL-8, Hu IP-10/CXCL10, Hu I-TAC/CXCL11, Hu MCP-1/CCL2, Hu MCP-2/CCL8, Hu MCP-3/CCL7, Hu MCP-4/CCL13, Hu MDC/CCL22, Hu MIF, Hu MIG/CXCL9, Hu MIP-1a/CCL3, Hu MIP-1d/CCL15, Hu MIP-3a/CCL20, Hu MIP-3b/CCL19, Hu MPIF-1/CCL23, Hu SCYB16/CXCL16, Hu SDF1a+b/CXCL12, Hu TARC/CCL17, Hu TECK/CCL25, and Hu TNF-a.

In some embodiments, the detected biological molecule(s) include one or more of the following: Hu Eotaxin, Hu FGF basic, Hu G-CSF, Hu GM-CSF, Hu IFN-g, Hu IL-10, Hu IL-12 (p70), Hu IL-13, Hu IL-15, Hu IL-17, Hu IL-1b, Hu IL-1ra, Hu IL-2, Hu IL-4, Hu IL-5, Hu IL-6, Hu IL-7, Hu IL-8, Hu IL-9, Hu IP-10, Hu MCP-1(MCAF), Hu MIP-1a, Hu MIP-1b, Hu PDGF-bb, Hu RANTES, Hu TNF-a, and Hu VEGF. In some embodiments, the test agent inhibits epithelial-mesenchymal transition (EMT). In some embodiments, the test agent is a small molecule compound. In some embodiments, the methods described herein are used to screen a library of test agents, for example, a library of chemical compounds. In some embodiments, the test agent comprises a nucleic acid molecule, for example, a DNA molecule, an RNA molecule, or a DNA/RNA hybrid molecule, single-stranded, or double-stranded. In some embodiments, the test agent comprises an RNAi agent, for example, an antisense-RNA, an siRNA, an shRNA, a snoRNA, a microRNA (miRNA), or a small temporal RNA (stRNA). In some embodiments, the test agent comprises an aptamer. In some embodiments, the test agent comprises a protein or peptide. In some embodiments, the test agent comprises an antibody or an antigen-binding antibody fragment, e.g., a F(ab')2 fragment, a Fab fragment, a Fab' fragment, or an scFv fragment. In some embodiments, the antibody is a single domain antibody. In some embodiments, the agent comprises a ligand-or receptor-binding protein. In some embodiments, the agent comprises a gene therapy vector.

In some embodiments, more primary tumor cell spheroids are cultured in the presence of more than one agent, e.g., a first test agent and a second test agent, optionally a third test agent, fourth agent, etc.

In some embodiments, a test agent is an anti-cancer agent. In some embodiments a test agent is a chemotherapeutic agent, an immunomodulatory agent, or radiation.

Exemplary chemotherapeutic agents include asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, a test agent is a vinca alkaloid, e.g., vinblastine, vincristine, vindesine, vinorelbine. In some embodiments, a test agent is an alkylating agent, e.g., cyclophosphamide, decarbazine, melphalan, ifosfamide, temozolomide. In some embodiments, a test agent is an antimetabolite, e.g., folic acid antagonists, pyrimidine analogs, purine analogs or adenosine deaminase inhibitor, e.g., fludarabine. In some embodiments, a test agent is an mTOR inhibitor. In some embodiments, a test agent is a proteasome inhibitor, e.g., aclacinomycin A, gliotoxin or bortezomib.

Exemplary immunomodulatory agents include immune activating agents or inhibitors of an immune checkpoint protein selected from the group consisting of: CTLA-4, PD-1, PDL-1, TIM3, LAG3, B7-H3 (CD276), B7-H4, 4-1BB (CD137), OX40, ICOS, CD27, CD28, PDL-2, CD80, CD86, B7RP1, HVEM, BTLA, CD137L, OX40, CD70, CD40, CD40L, GAL9, A2aR, and VISTA. In some embodiments, the immune checkpoint inhibitor is a peptide, antibody, interfering RNA, or small molecule. In some embodiments, the immune checkpoint inhibitor, e.g., inhibitor, is a monoclonal antibody, or an Ig fusion protein. In some embodiments, the immune checkpoint inhibitor is an antibody or an antigen binding fragment thereof. In some embodiments, the immune checkpoint inhibitor an anti-PD-1 antibody.

In some embodiments, the immune checkpoint inhibitor inhibits PD1. In some embodiments, the immune checkpoint inhibitor inhibits CTLA-4. In some embodiments, the immune checkpoint inhibitor inhibits TIM-3. In some embodiments, the immune checkpoint inhibitor inhibits LAG-3. In some embodiments, the immune checkpoint inhibitor inhibits VISTA.

In some embodiments, a combination of test agents are tested in the cell culture. In some embodiments, the combination of immune checkpoint inhibitors includes a PD1 inhibitor and a CTLA-4 inhibitor. In some embodiments, the combination of immune checkpoint inhibitors includes a PD1 inhibitor and a TIM-3 inhibitor. In some embodiments, the combination of immune checkpoint inhibitors includes a PD1 inhibitor and a LAG-3 inhibitor. In some embodiments, the combination of immune checkpoint inhibitors includes a CTLA-4 inhibitor and a TIM-3 inhibitor. In some embodiments, the combination of immune checkpoint inhibitors includes a CTLA-4 inhibitor and a LAG-3 inhibitor. In some embodiments, the combination of immune checkpoint inhibitors includes a TIM-3 inhibitor and a LAG-3 inhibitor. In some embodiments, the combination of immune checkpoint inhibitors includes a PD1 inhibitor , a CTLA-4 inhibitor, and a TIM-3 inhibitor. In some embodiments, the combination of immune checkpoint inhibitors includes a PD1 inhibitor, a CTLA-4 inhibitor , and a LAG-3 inhibitor. In some embodiments, the combination of immune checkpoint inhibitors includes a PD1 inhibitor, a TIM-3 inhibitor, and a LAG-3 inhibitor. In some embodiments, the combination of immune checkpoint inhibitors includes a CTLA-4 inhibitor, a TIM-3 inhibitor , and a LAG-3 inhibitor.

In some embodiments, an immune activating agent is a CD28 antagonist, e.g., an anti-CD28 antibody.

In some embodiments, a test agent is a small molecule inhibitor, e.g., a TBK1 inhibitor, a MEK inhibitor, a FAK inhibitor, a BRD/BET inhibitor, a CDK 4/6 inhibitor, an HDAC inhibitor, a DNMT inhibitor (or hypomethylating agent), a MET inhibitor, an EGFR inhibitor, or a BRAF inhibitor. In some embodiments, a test agent is a kinase inhibitor, e.g., a TBK1 inhibitor, a MEK inhibitor, a FAK inhibitor, or a CDK 4/6 inhibitor.

In some embodiments, the proliferation and/or dispersion of the tumor cell spheroids is reduced in the presence of the test agent as compared to the absence of the agent, indicating that the agent can be used to treat cancer. In some embodiments, the proliferation and/or dispersion of the tumor cell spheroids is reduced in the presence of the test agent as compared to the absence of the agent by at least 10%, 25%, 50%, 75%, 90%, 95% or 100%.

In some embodiments, the size and/or number of cells of the tumor cell spheroids is reduced in the presence of the test agent as compared to the absence of the agent, indicating that the agent can be used to treat cancer. In some embodiments, the size and/or number of cells of the tumor cell spheroids is reduced in the presence of the test agent as compared to the absence of the agent by at least 10%, 25%, 50%, 75%, 90%, 95% or 100%.

In some embodiments, a change in the secretion of a biological molecule into the cell culture supernatant in the presence of the test agent as compared to the absence of the agent is indicative that the agent can be used to treat cancer. In some embodiments, the secretion of a biological molecule into the cell culture supernatant, e.g., a change which is indicative of immune activation, is increased in the presence of the test agent as compared to the absence of the agent by at least 10%, 25%, 50%, 75%, 90%, 95% or 100%, indicating that the agent can be used to treat cancer. In some embodiments, the secretion of a biological molecule into the cell culture supernatant, e.g., a change which is indicative of immune suppression, is reduced in the presence of the test agent as compared to the absence of the agent by at least 10%, 25%, 50%, 75%, 90%, 95% or 100%, indicating that the agent can be used to treat cancer.

In some embodiments, cells can be liberated from the cell culture device, e.g., by collagenase. The liberated cells can be subjected to analyses such as, for example, flow cytometry, immunofluorescence, among others.

In some aspects, a subject can be treated with an agent identified as useful for treating cancer according to a method described herein. For example, in some embodiments, the present disclosure provides a method for treating cancer in a subject, the method comprising: a) obtaining a tumor sample from the subject; b) identifying an agent that can be used to treat cancer in the subject according to a method described herein; and c) administering the agent to the subject.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods
Freezing Medium:
　1 mL DMEM (w/10% FBS, 1× Antibiotic/Antimycotic, 1× L-Glutamine)
　8 mL FBS
　1 mL DMSO
　Sterile Filter with 0.22 um syringe filter if all components are not sterile
Matrigel
　BD Biosciences 'BD Matrigel™ Matrix Basement Membrane' (Part number 354234). NB: Thaw completely overnight @ 4° C. the aliquot which you will be using; always keep cold, using pre-cooled tubes, tips, and syringes (it gels at temps slightly above Room Temp).
Collagen Type I
BD Biosciences
Preparation of 1,000× Insulin(10 mg/mL):
　50 mg of powder (one bottle)+5 mL of 6 μM HCl
Recipe for 1× Collagenase Buffer Solution:
　DMEM/F12 or RPMI with 15 mM HEPES containing:
　FBS (5%)
　Insulin (10 ng/mL)
　EGF(10 ng/mL)
　Hydrocortisone(10 μg/mL)
　Pen/Strep/Fung(1×)
　Collagenase(0.5 mg/mL)
Preparation of 500 mLs of Collagenase Buffer Solution (for Overnight Dissociation)
　DMEM/F12 with 15 mM HEPES: 500 mL
　Calf serum or FBS: 25 mL (5%)
　1,000× Insulin: 500 μl(final con: 10 ng/mL)
　Pen/Strep/Fung(100×): 5 mL
　Hydrocortisone (final con: 10 μg/mL):
　Collagenase (final con: 0.5 mg/mL)

Generation of Spheroids
1. To generate spheroids, the human primary tissues (fresh mesothelioma or PDX samples) were collected in media (RPMI) with 10% FBS.
2. Mince samples into tiny pieces on ice (approximately 1 mm). Then transfer the minced samples back on ice in a 50 mL conical tube containing 20 mL media. Spin tissue down at 800 rpm for 2 min and remove supernatant.
3. Collagenase the samples in collagenase buffer solution (see materials). Time of incubation ranged from 2 hours (fresh mesothelioma sample) or up to 12 hours (PDX breast sample) at 37 degrees Celsius (on a rotator in the dark if available) incubator.
4. Spin down the solution at 1000 rpm for 5 min and discard the supernatant.
5. Wash the samples 2 times: by adding 30 mL of PBS, re-suspending the samples, and then spin down the samples at 1000 rpm for 5 min, discarding the supernatant.
6. Re-suspended pellet in 20 mL fresh media, pipette up and down for 2-3 minutes (mix them well by 25 mL surgical pipette).
7. Individual spheroids were sieved via 100 μm and 40 μm cell strainers to yield spheroids 40-100 μm in diameter.
8. Harvest the spheroids from 40 μm strainer with 10 mL fresh media and centrifuged to separate them from the supernatant.

Tissue Freezing Procedure:
1. Freezing was performed from either directly minced tissue (PDX was minced and frozen in 90% FBS and 10% DMSO at −80° C.) or after tumor spheroids were harvested.
2. For freezing of tumor spheroids, spheroids from step 8 were centrifuged at 1000 rpm for 3 min.
3. Aspirate Medium.
4. Resuspend spheroids in 1 mL freezing medium (see appendix) per ampule to be frozen.
5. Aliquot samples into labeled ampules and put at −80° C. overnight.
6. Transfer cells the next day into liquid nitrogen for storage.

Thawing Procedure:
1. Remove tissue spheroid samples from liquid nitrogen and immediately place in 37° C. water bath to thaw quickly.
2. Resuspend spheroids from each vial in 35 mL DMEM Media with 10% FBS, 1× Antibiotic/Antimycotic, 1× L-Glutamine.
3. Spin down spheroids and re-suspend in collagen or matrigel for injection into the devices.

Results
Culture Device Fabrication and Tissue Implantation in 3D Matrix

Figure 2:
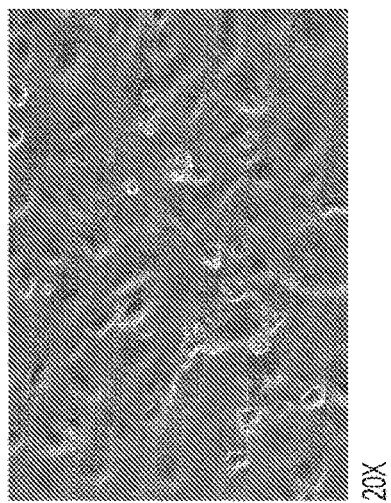
FIG. 2 shows co-culture of mesothelioma spheroids with HUVECs.
Figure 2:
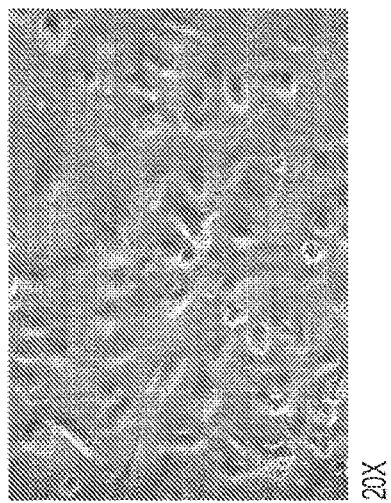
Figure 2:
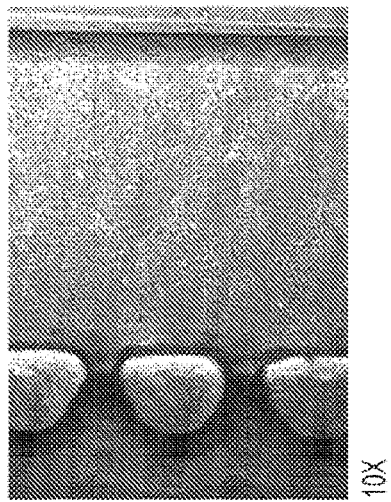
Figure 3:
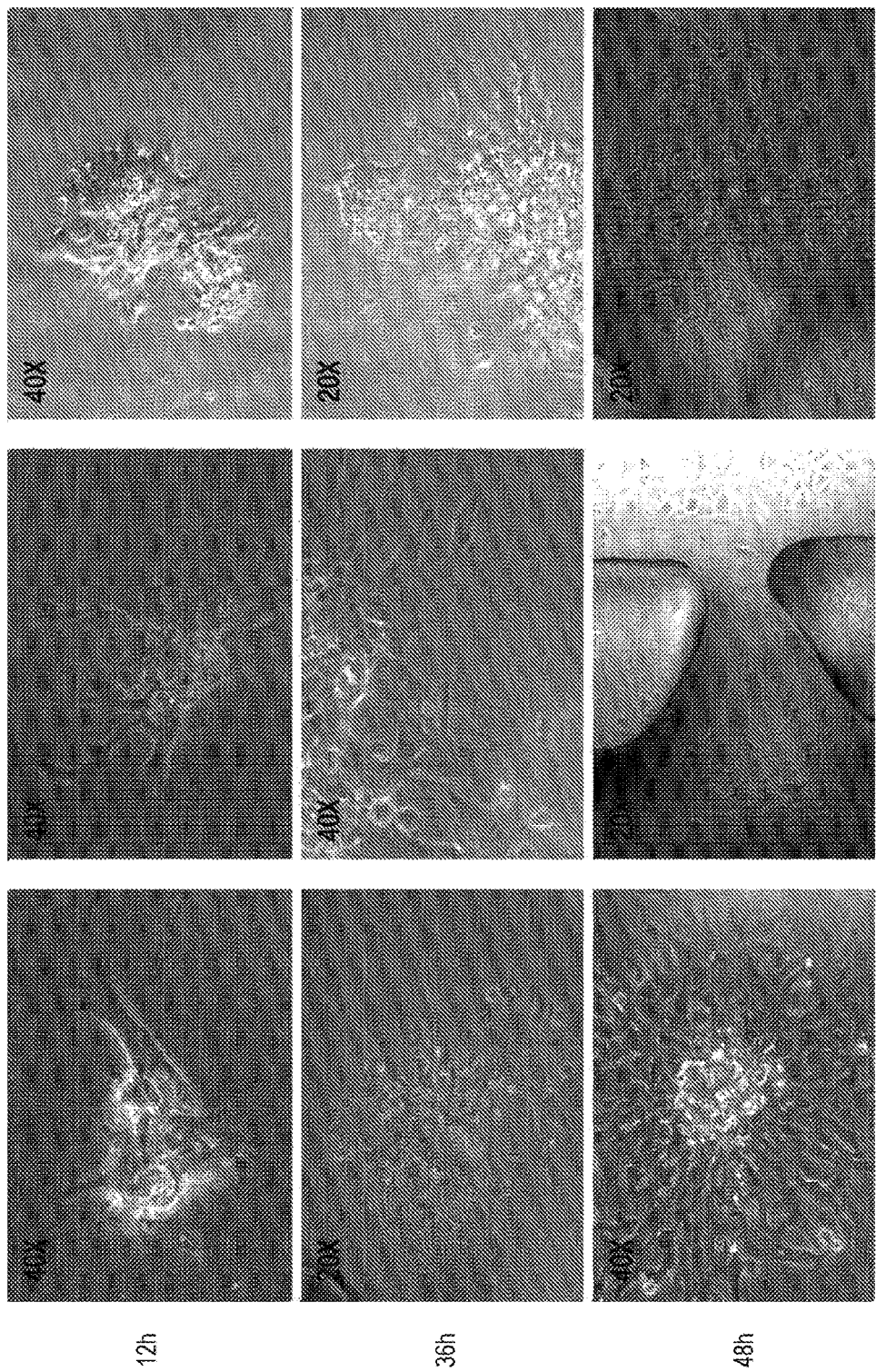
FIG. 3 shows mesothelioma cell dissemination in 3-D culture over a period of 48 hours.

One embodiment of a three dimensional microfluidic culture device was fabricated according to the disclosures of Aref et al., Integrative Biology 2013; PMID 23172153 and US published patent application US 2014-0057311 A1 (each herein incorporated by reference in its entirety). Mesothelioma spheroids were generated from primary tumor tissue, frozen, thawed, and implanted into the device, by the methods described herein. Spheroids were visualized in the device by immunofluorescence confocal microscopy, as shown in FIG. 1. In another experiment, spheroids were co-cultured with human umbilical vein endothelial cells (HUVECs) in the device, as shown in FIG. 2. FIG. 3 shows confocal microscopy pictures depicting mesothelioma cell dissemination in 3 dimensions over a period of 48 hours after implantation into the device.

References

1. Tentler J J, Tan A C, Weekes C D, Jimeno A, Leong S, Pitts T M, et al. Patient-derived tumour xenografts as models for oncology drug development. Nature reviews Clinical oncology. 2012; 9(6):338-50. Epub Apr. 18, 2012. doi: 10.1038/nrclinonc.2012.61. PubMed PMID: 22508028; PubMed Central PMCID: PMC3928688.
2. Aref A R, Huang R Y, Yu W, Chua K N, Sun W, Tu T Y, et al. Screening therapeutic EMT blocking agents in a three-dimensional microenvironment. Integrative biology: quantitative biosciences from nano to macro. 2013; 5(2): 381-9. Epub Nov. 11, 2012. doi: 10.1039/c2ib20209c. PubMed PMID: 23172153.
3. Zhu Z, Aref A R, Cohoon T J, Barbie T U, Imamura Y, Yang S, et al. Inhibition of KRAS-Driven Tumorigenicity by Interruption of an Autocrine Cytokine Circuit. Cancer discovery. 2014; 4(4):452-65. Epub Jan. 22, 2014. doi: 10.1158/2159-8290.CD-13-0646. PubMed PMID: 24444711.
4. Yu M, Bardia A, Aceto N, Bersani F, Madden M W, Donaldson M C, et al. Cancer therapy. Ex vivo culture of circulating breast tumor cells for individualized testing of drug susceptibility. Science. 2014; 345(6193):216-20. Epub Jul. 12, 2014. doi: 10.1126/science.1253533. PubMed PMID: 25013076.
5. Gao D, Vela I, Sboner A, Iaquinta P J, Karthaus W R, Gopalan A, et al. Organoid cultures derived from patients with advanced prostate cancer. Cell. 2014; 159(1):176-87. Epub Sep. 10, 2014. doi:10.1016/j.cell.2014.08.016. PubMed PMID: 25201530.
6. Gerdes M J, Sevinsky C J, Sood A, Adak S, Bello M O, Bordwell A, et al. Highly multiplexed single-cell analysis of formalin-fixed, paraffin-embedded cancer tissue. Proceedings of the National Academy of Sciences of the United States of America. 2013; 110(29):11982-7. Epub Jul. 3, 2013. doi: 10.1073/pnas.1300136110. PubMed PMID: 23818604; PubMed Central PMCID: PMC3718135.
7. Yao Z, Fenoglio S, Gao D C, Camiolo M, Stiles B, Lindsted T, et al. TGF-beta IL-6 axis mediates selective and adaptive mechanisms of resistance to molecular targeted therapy in lung cancer. Proceedings of the National Academy of Sciences of the United States of America. 2010; 107(35):15535-40. Epub Aug. 18, 2010. doi: 10.1073/pnas.1009472107. PubMed PMID: 20713723; PubMed Central PMCID: PMC2932568.
8. Seguin L, Kato S, Franovic A, Camargo M F, Lesperance J, Elliott K C, et al. An integrin beta(3)-KRASRalB complex drives tumour stemness and resistance to EGFR inhibition. Nature cell biology. 2014; 16(5):457-68. Epub Apr. 22, 2014. doi: 10.1038/ncb2953. PubMed PMID: 24747441.

Example 2

3D Culture of Spheroids

The overview of an exemplary method of 3D culture of spheroids is shown in Table 1.

TABLE 1

| Day −1 | Device fabrication/preparation* |
| Day 1 | Sample collection, collagenase digestion, spheroid filtration/collection |
| Day 2 | Spheroid collection/harvest, resuspension in collagen, loading device |

TABLE 1-continued

| | Collagen polymerization |
| | Addition of culture media |
| | Addition of endothelial cells |
| Day 3 | Treatment with test agent(s) |
| Day 5-6 | Collect conditioned media, e.g., for identification of secreted biological molecule(s), e.g., multiplex cytokine analysis |
| Day 6+ | Monitor cell growth, fix cells, immunostaining, RNAseq, flow cytometry |

On Day 1, tumor was collected in an operating room and placed in a sterile 15 mL conical tube bathed with culture media (10% FBS with DMEM or RPMI) and stored on ice. The media was aspirated in a sterile hood and the tumor specimen gently placed in a normal 10 cm culture dish on ice. Using a scalpel, the tumor was minced into smaller pieces. A sample can optionally be exposed to strong collagenase treatment to generate single cells that can be submitted directly for flow cytometry. To the 10 cm dish containing the minced tumor was added 10 mL of collagenase solution (10 mL media, 150 μL HEPES (15 mM final concentration), 100 μL collagenase (100 U/μL stock, 1 unit/μL final concentration)). The minced tumor and collagenase mixture was subsequently transferred to a 50 mL conical tube, and then transferred to a fresh low-attachment 10 cm dish. The low-attachment dish comprising the sample was incubated at 37° C. for 30-60 minutes while checking every 15-30 minutes, as the duration of time required varies from specimen to specimen. The intended outcome of this step is to generate multicellular spheroids via a limited collagenase digestion, so the sample should not be comprised entirely of single cells. After the 45-60 minute incubation period, 10 mL of fresh media was added to the dish containing the tumor sample and the contents (~20 mL) transferred to a 50 mL conical tube. The solid tumor and tumor spheroids were then pelleted via centrifugation at 1200-1300 rpm for 4-5 minutes. The resulting supernatant was transferred to a new tube for future re-use of the collagenase solution, and the pellet was resuspended in 10-20 mL media (e.g., 10% FBS/DMEM) using a 25 mL pipet. The media containing the solid tumor and tumor spheroids was passed over a 100 μm filter that was resting on a 50 mL conical tube. The filter, which had captured residual tumor and spheroids greater than 100 μm, was inverted, rinsed with residual collagenase-media solution, transferred to "Dish 1," and returned to the 37° C. incubator. This step can be performed to recover additional spheroids on Day 2 after continued, limited collagenase digestion. The flow-through from the 100 μm filter was passed over a 40 μm filter that was resting on a fresh 50 mL conical tube. The 40 μm filter was inverted and the cells were recovered by passing 10 mL media (10% FBS/DMEM) over the filter and collecting cells into a 10 cm low attachment petri dish ("Dish 2," 40-100 μm). The flow-through from the 40 μm filter was placed in a separate 10 cm dish ("Dish 3," <40 μm, mostly single cells), and returned to 37° C. overnight. Spheroids can be immediately loaded into the 3D culture devices or kept in culture overnight.

On Day 2, the spheroids in Dish #2 were examined under a microscope. A collagen solution (150 μL rat tail collagen (type I), 20 μL 10× PBS, 7 μL 1 N NaOH, 23 μL sterile $H_2O$) was prepared on ice. The media and spheroids from Dish #2 were collected and the spheroids pelleted at 1100 rpm for 2 minutes. The media was aspirated and the 15 mL conical tubes containing cell pellets were placed on ice. The cell pellets were resuspended on ice via the addition of 200 μL (or more as needed) of collagen mixture. During this procedure, care was taken to limit the amount of time the pellet was not on ice. Approximately 15-20 µL of spheroid-collagen mixture per device was added at either end of the gel channel. The 3D devices were placed in humidified, sterile containers for 45-60 min at 37° C. After approximately 1 hour, ~200 µL of the appropriate culture media were added to hydrate the devices and provide a nutrition and growth factor source to the spheroids, and the devices were returned to 37° C. incubation. While the polymerized collagen-spheroid mixture was being hydrated with media, HUVEC were trypsinized, cells were pelleted and resuspended in 50-100 µL of EGM2 media and loaded to the LEFT media channel. Alternatively, spheroids can be grown in the absence of HUVEC.

On Day 3, media was aspirated from the device and ~200 µL media (1:1 mixture of 10% FBS-DMEM and EGM2 supplemented with growth factors per protocol) with or without treatment (e.g., anti-PD-1 monoclonal Ab) were added to each device. The devices were subsequently placed in humidified, sterile containers, and returned to 37° C. incubation.

On Day 6 (or 48-72 hours post-treatment), conditioned media was collected for cytokine analysis. Light microscopy was performed and images obtained to characterize and document spheroid dispersal and/or putative immune response, which is commonly characterized by non-pigmented cells surrounding the brown-pigmented melanoma spheroids. Media was collected from each device by aspiration using a 200 µL pipet, transferred to sterile 1.5 mL Eppendorf tubes, and frozen at −80° C. prior to submission to CMOP for multiplex cytokine/chemokine analysis. Also on Day 6, the cells present in the 3D culture device following treatment were characterized by multiple methods.

For flow cytometry, RNA sequencing analysis, or T-cell receptor (TCR) sequencing the cells were removed using collagenase (150 µL per device) after media had been removed. The mixture was then incubated for 20-25 minutes until the spheroids began to demonstrate movement within the 3D device by light microscopy. The cells in collagenase were aspirated into a 15 mL conical tube containing 4.0 mL of sterile 1× PBS and spun down for 5 minutes at 1100 rpm. The PBS wash was gently aspirated and the pellet resuspended in 1.5 mL 10% FBS-DMEM for flow cytometry. In some instances, genomic DNA is prepared from flow-sorted T lymphocytes for TCR sequencing using the ImmunoSeq platform from Adaptive Biotechnologies to evaluate T-cell receptor clonality. Clonality can be assessed in spheroids relative to bulk tumor, and in response to immune checkpoint blockade to evaluate for increased TCR clonality (indicating expansion of tumor-reactive T cell clones). For RNA sequencing, the resuspension can be performed using 1.5 mL 10% FBS-DMEM, PBS, or a compatible lysis buffer.

For direct immunofluorescence analysis, a fixing step was first performed after media had been removed. In this step, 200 µL of 4% paraformaldehyde was added to each device via gel and side ports and incubated for 15 minutes at room temp. Following the incubation period, paraformaldehyde was removed and 200 µL of 0.1% Triton X-100 was added for permeabilization and allowed to incubate for 10 minutes at room temperature. Triton X-100 was then removed and the device washed with 1× PBS 2-3 times. Next, 200 µL, of 5% FBS in PBS was added to each device followed by a 30-60 minute incubation period at room temp. An appropriate dilution of primary antibody in 5% FBS-PBS was added and followed by overnight incubation at 4° C. After the incubation period, primary antibody was removed and washed with 1× PBS 2-3 times. The secondary antibody was added as 1:500 Alexa-Fluor antibody in 5% FBS-PBS and incubated for 2-4 hours at room temperature, with care taken to avoid or minimize sample exposure to light. The secondary antibody was then removed and washed with 1× PBS 2-3 times. Approximately 200 µL PBS was kept in device as fixed/stained devices can be directly visualized by fluorescence microscopy or stored at 4° C. until they are visualized.

Example 3

Immunotherapy with PD-1 blockade is associated with significant activity in patients with metastatic melanoma, but durable responses are only observed in a limited number of patients. To date there are no proven biomarkers or patient characteristics that reliably predict response to immune checkpoint inhibitors. PD-L1 expression predicts response to anti-PD-1/PD-L1 antibodies in some, but not all patients, and is increasingly recognized as an imperfect marker of activity. As biopsies from patients who have responded to these agents often demonstrate the presence of an inflammatory infiltrate within the tumor, and gene expression profiling studies have confirmed upregulation of pro-inflammatory cytokines and chemokines within tumors following PD-1 blockade, there is increasing interest in understanding the role of the tumor microenvironment in the response to immune checkpoint inhibition. Unfortunately, most approaches to evaluate the tumor microenvironment rely on fixed tissue from biopsies, which precludes dynamic evaluation of features associated with response.

A microfluidic cell culture technology has been previously used to study drug sensitivity of tumor cell line spheroids and was also shown to support the growth of primary human tumor specimens. The technology recapitulates the tumor microenvironment, incorporating a model extracellular matrix (ECM), enabling cell-cell interactions that reflect the endothelial and/or immune-cancer cell interface, and allowing controlled analysis of growth factor and cytokine mediated effects. The advantages of this system provided a basis for its use in examining the consequences of PD-1 blockade ex vivo. In some embodiments, melanoma served as the cancer model as it exhibits a relatively high response rate to anti-PD1 antibodies and also produces melanocyte pigments that function as tumor cell-specific markers.

Figure 4:
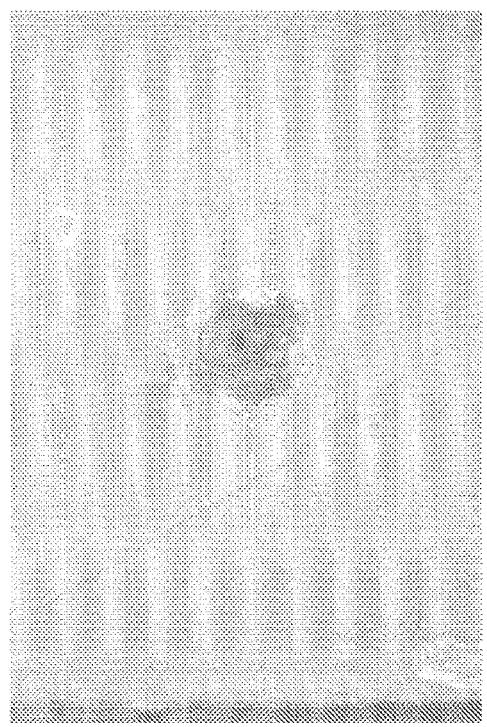
FIG. 4 depicts an exemplary immune response in melanoma spheroids exposed to anti-PD1 in the absence and presence of anti-CD28 co-stimulation.
Figure 4:
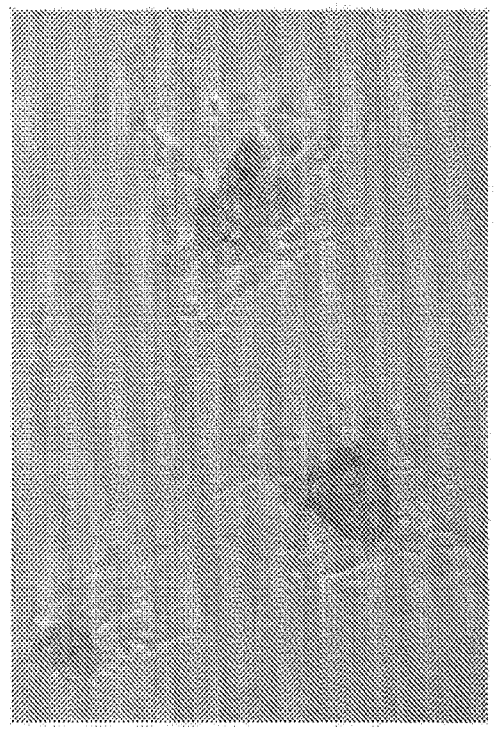
Figure 5:
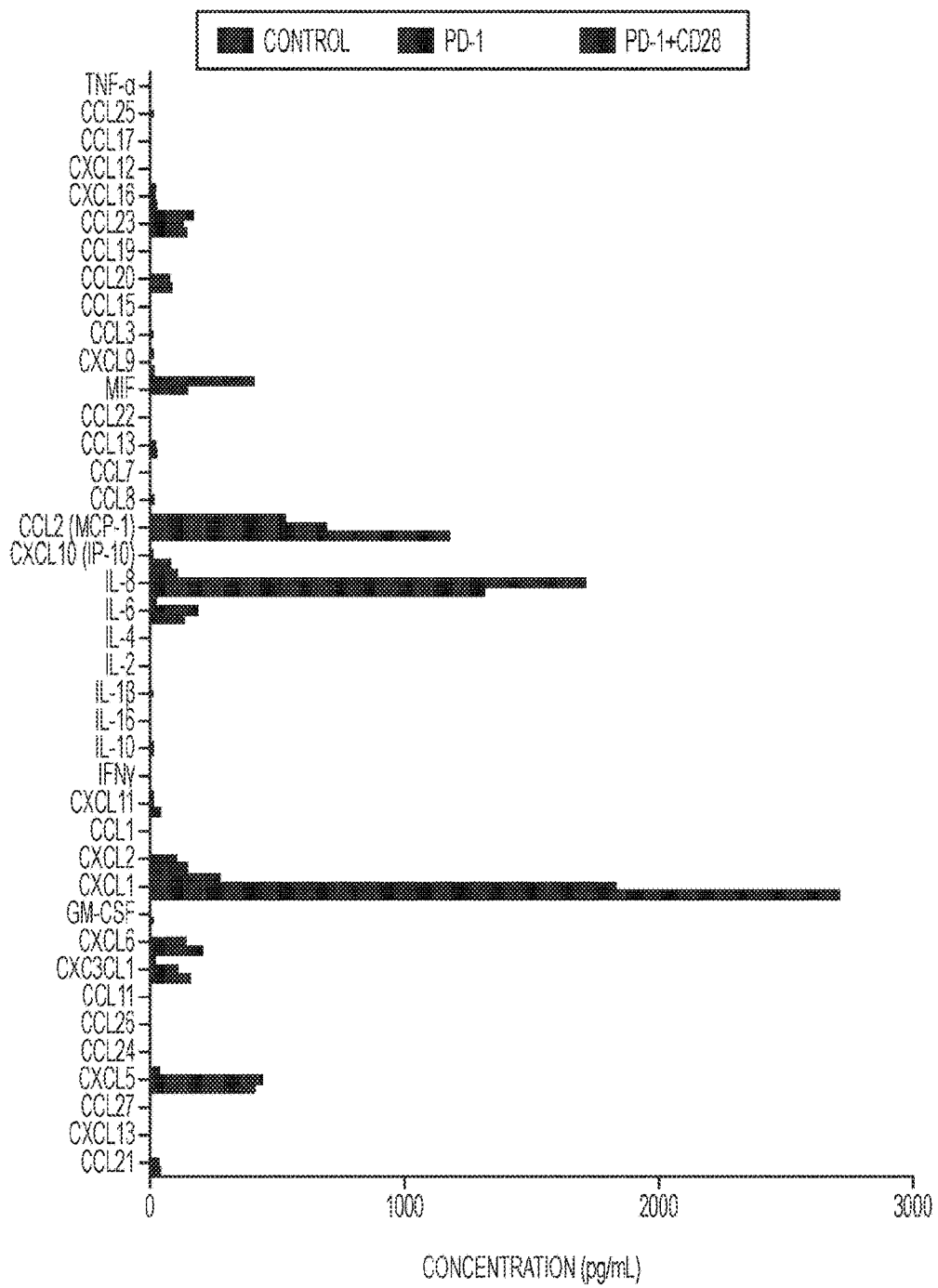
FIG. 5 depicts an exemplary cytokine profile for aPD1 exposure and αPD1 in combination with anti-CD28.

In spheroids derived from multiple different melanoma resection specimens, there was an observed immune response to anti-PD1 (pembrolizumab 250 µg/mL) exposure in the absence (FIG. 4A) and presence (FIG. 4B) of anti-CD28 co-stimulation. As the spheroids and co-cultured endothelial cells are bathed in media, the conditioned media was extracted from the device and luminex cytokine profiling was performed. There was an observed pronounced up-regulation of multiple cytokines specifically following αPD1 exposure, and certain cytokines (e.g., IP10), which were induced by the combination with anti-CD28 (FIG. 5). Together, these findings demonstrated the ability of this system to capture an immune response to PD1 blockade ex vivo, and quantify unique cytokine profiles.

Additionally, although it was demonstrable by flow cytometry of melanoma tumor spheroids at baseline that they consisted of up to 20% immune cells, including T cells, dendritic cells, monocytes (not shown), the value of extracting cells from the device and repeating flow cytometry post-treatment was realized. By repeating collagenase digestion within the device and washing cells in PBS, conditions have been developed that enable repeat immune profiling.

Figure 6:
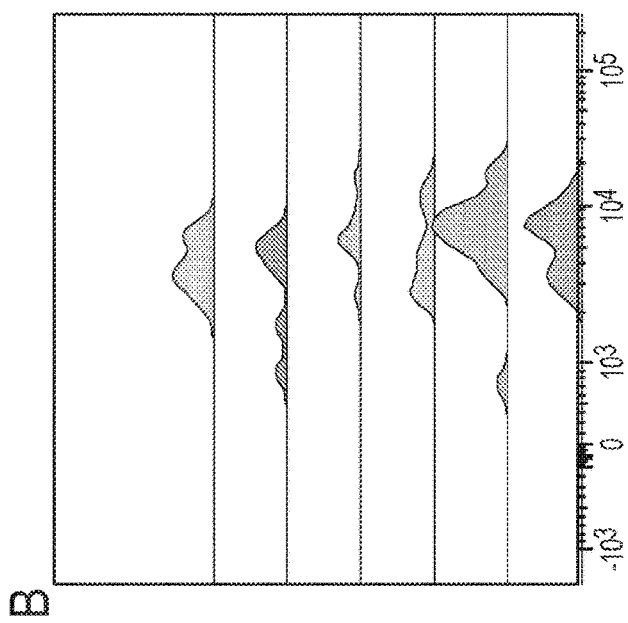
FIG. 6 depicts an exemplary immune profiling of treated samples.
Figure 6:
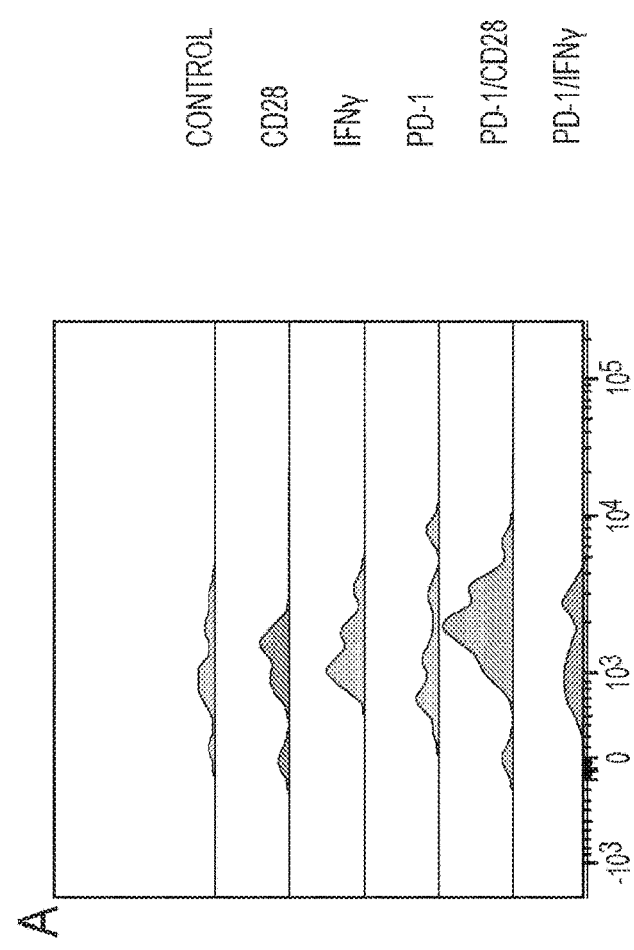

Interestingly, following anti-PD1 or especially anti-PD1/anti-CD28 treatment, there was an observed increase in markers of early CD8 T cell activation such as CD69 (FIG. 6A), which was accompanied by an increase in specific immune checkpoint receptors such as TIM3 (FIG. 6B). Thus, in addition to characterizing differential secreted cytokine profiles, the microfluidic culture system provides the capacity to study the impact of checkpoint blockade on the activation of T cells and other immune populations in real time on primary patient tumor specimens.

1. Lo J A, Fisher D E. The melanoma revolution: from UV carcinogenesis to a new era in therapeutics. Science. 2014; 346(6212):945-9. Epub Nov. 22, 2014. doi: 10.1126/science.1253735. PubMed PMID: 25414302.
2. Carbognin L, Pilotto S, Milella M, Vaccaro V, Brunelli M, Calio A, Cuppone F, Sperduti I, Giannarelli D, Chilosi M, Bronte V, Scarpa A, Bria E, Tortora G. Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. 2015; 10(6): e0130142. doi: 10.1371/journal.pone.0130142. PubMed PMID: 26086854; PMCID: 4472786.
3. Taube J M, Young G D, McMiller T L, Chen S, Salas J T, Pritchard T S, Xu H, Meeker A K, Fan J, Cheadle C, Berger A E, Pardoll D M, Topalian S L. Differential Expression of Immune-Regulatory Genes Associated with PD-L1 Display in Melanoma: Implications for PD-1 Pathway Blockade. Clin Cancer Res. 2015; 21(17):3969-76. doi: 10.1158/1078-0432.CCR-15-0244. PubMed PMID: 25944800.
4. Aref A R, Huang R Y, Yu W, Chua K N, Sun W, Tu T Y, Bai J, Sim W J, Zervantonakis I K, Thiery J P, Kamm R D. Screening therapeutic EMT blocking agents in a three-dimensional microenvironment. Integr Biol (Camb). 2013; 5(2):381-9. doi: 10.1039/c2ib20209c. PubMed PMID: 23172153; PMCID: 4039387.
5. Zhu Z, Aref A R, Cohoon T J, Barbie T U, Imamura Y, Yang S, Moody S E, Shen R R, Schinzel A C, Thai T C, Reibel J B, Tamayo P, Godfrey J T, Qian Z R, Page A N, Maciag K, Chan E M, Silkworth W, Labowsky M T, Rozhansky L, Mesirov J P, Gillanders W E, Ogino S, Hacohen N, Gaudet S, Eck M J, Engelman J A, Corcoran R B, Wong K K, Hahn W C, Barbie D A. Inhibition of KRAS-driven tumorigenicity by interruption of an autocrine cytokine circuit. Cancer Discov. 2014; 4(4):452-65. doi: 10.1158/2159-8290.CD-13-0646. PubMed PMID: 24444711; PMCID: 3980023.

We claim:

1. A method for culturing patient-derived tumor cell spheroids in a three-dimensional microfluidic device, the method comprising:
   mincing a primary tumor sample in a medium supplemented with serum;
   treating the minced primary tumor sample with a composition comprising an enzyme;
   collecting tumor spheroids having a diameter of 10 µm to 500 µm from the enzyme treated sample;
   suspending the tumor spheroids in biocompatible gel; and
   culturing the tumor spheroids in a three dimensional microfluidic device.

2. The method of claim 1, wherein the minced primary tumor sample is frozen in a medium supplemented with serum and thawed prior to treating with the composition comprising the enzyme.

3. The method of claim 1, wherein the collected tumor spheroids are frozen in a freezing medium and then thawed before suspending in the biocompatible gel.

4. The method of claim 1, wherein the minced primary tumor sample comprises tumor pieces in the size of about 1 mm.

5. The method of claim 1, wherein the tumor spheroids having a diameter of 10 µm to 500 µm are collected from the enzyme mix treated sample with the use of a sieve.

6. The method of claim 1, wherein the tumor spheroids having a diameter of 10 µm to 500 µm are collected by sieving the enzyme mix treated sample via 500 µm and 10 µm cell strainers to yield tumor spheroids having a diameter of 10 µm to 500 µm.

7. The method of claim 1, wherein the enzyme is collagenase.

8. The method of claim 1, wherein the composition comprising the enzyme comprises a serum-supplemented culture medium, insulin, a corticosteroid, an antibiotic, collagenase and optionally a growth factor.

9. The method of claim 1, wherein the minced primary tumor sample is treated with the composition comprising the enzyme in an amount or for a time sufficient yield a partial digestion of the minced primary tumor sample.

10. The method of claim 1, wherein the minced primary tumor sample is treated with the composition comprising the enzyme for 30 minutes to 15 hours at a temperature of 25° C. to 39° C.

11. The method of claim 1, wherein the three dimensional microfluidic device comprises:
   one or more fluid channels flanked by one or more gel cage regions, wherein the one or more gel cage regions comprises the biocompatible gel in which the tumor spheroids are embedded, and wherein the device recapitulates in vivo tumor microenvironment.

12. The method of claim 1, wherein the three dimensional microfluidic device comprises:
   a substrate comprised of an optically transparent material and further comprising
   i) one or more fluid channels;
   ii) one or more fluid channel inlets;
   iii) one or more fluid channel outlets;
   iv) one or more gel cage regions; and
   v) a plurality of posts;
wherein all or a portion of each gel cage region is flanked by all or a portion of one or more fluid channels, thereby creating one or more gel cage region-fluid channel interface regions; each gel cage region comprises at least one row of posts which forms the gel cage region; and the one or more gel cage region has a height of at least 500 µm.

13. The method of claim 12, wherein the one or more gel cage region has a height sufficient for at least 200-1000 µm above the tumor cell spheroids.

14. The method of claim 12, wherein the gel cage region has a cuboidal shape.

15. The method of claim 1, wherein the tumor spheroids are cultured in the presence and absence of a test agent.

16. The method of claim 1, further comprising detecting a change in the tumor cell spheroid culture indicative of a condition that is likely to reduce proliferation and/or dispersion of the tumor cell spheroids in the presence of the first test agent as compared to the absence of the first test agent.

* * * * *